(12) United States Patent
Kollatschny et al.

(10) Patent No.: US 8,509,914 B2
(45) Date of Patent: Aug. 13, 2013

(54) INSERT FOR IMPLANTABLE ELECTRODE

(75) Inventors: Shawn D. Kollatschny, Pearland, TX (US); Joseph J. Sciacca, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 758 days.

(21) Appl. No.: 11/261,102

(22) Filed: Oct. 28, 2005

(65) Prior Publication Data

US 2007/0100406 A1    May 3, 2007

(51) Int. Cl.
    *A61N 1/05* (2006.01)
(52) U.S. Cl.
    USPC ............ 607/116; 607/117; 607/118; 607/119
(58) Field of Classification Search
    USPC .......................... 607/116–119; 600/393, 394
    See application file for complete search history.

(56) References Cited

U.S. PATENT DOCUMENTS

| | | | |
|---|---|---|---|
| 3,421,511 A | 1/1969 | Schwartz et al. | |
| 3,760,812 A | 9/1973 | Timm et al. | |
| 4,384,926 A | 5/1983 | Wagner | |
| 4,459,989 A | 7/1984 | Borkan | |
| 4,508,053 A | 4/1985 | Eriksson | |
| 4,573,481 A | 3/1986 | Bullara | |
| 4,590,946 A | 5/1986 | Loeb | |
| 4,608,985 A | 9/1986 | Crish et al. | |
| 4,612,934 A | 9/1986 | Borkan | |
| 4,628,942 A | 12/1986 | Sweeney et al. | |
| 4,649,936 A | 3/1987 | Ungar et al. | |
| 4,850,356 A | 7/1989 | Heath | |
| 4,860,616 A | 8/1989 | Smith | |
| 4,920,979 A | 5/1990 | Bullara | |
| 4,979,511 A | 12/1990 | Terry, Jr. | |
| 5,003,975 A | 4/1991 | Hafelfinger et al. | |
| 5,095,905 A | 3/1992 | Klepinski | |
| 5,215,089 A | 6/1993 | Baker, Jr. | |
| 5,251,634 A | 10/1993 | Weinberg | |
| 5,351,394 A | 10/1994 | Weinberg | |
| 5,531,778 A | 7/1996 | Maschino et al. | |
| 6,304,787 B1 | 10/2001 | Kuzma et al. | |
| 6,418,348 B1 | 7/2002 | Witte | |
| 6,473,653 B1 | 10/2002 | Schallhorn et al. | |
| 6,477,417 B1 | 11/2002 | Levine | |
| 6,600,956 B2 * | 7/2003 | Maschino et al. ............ 607/118 |
| 6,907,295 B2 | 6/2005 | Gross et al. | |
| 2004/0024440 A1 * | 2/2004 | Cole ............................ 607/122 |
| 2004/0167583 A1 | 8/2004 | Knudson et al. | |
| 2004/0172088 A1 | 9/2004 | Knudson et al. | |
| 2006/0058597 A1 | 3/2006 | Machado | |

\* cited by examiner

*Primary Examiner* — Joseph Stoklosa
(74) *Attorney, Agent, or Firm* — Cyberonics, Inc.

(57) ABSTRACT

A lead assembly comprises an outer body tubing, first and second conductors, and first and second tubing insert members. The outer body tubing comprises at least two longitudinal outer body tubing portions, each such portion comprising a through-hole and each portion comprising a keyed surface having a predetermined shape. Each of the tubing insert members receives a conductor and comprises a surface that substantially matches the predetermined shape of the keyed surface. When both of the conductors are inserted into corresponding longitudinal through-holes such that each of said first and second surfaces of the first and second hollow body members is substantially aligned with the keyed surface of a corresponding outer body tubing portion, electrodes formed on ends of the first and second conductors are encouraged to be substantially co-linear.

9 Claims, 9 Drawing Sheets

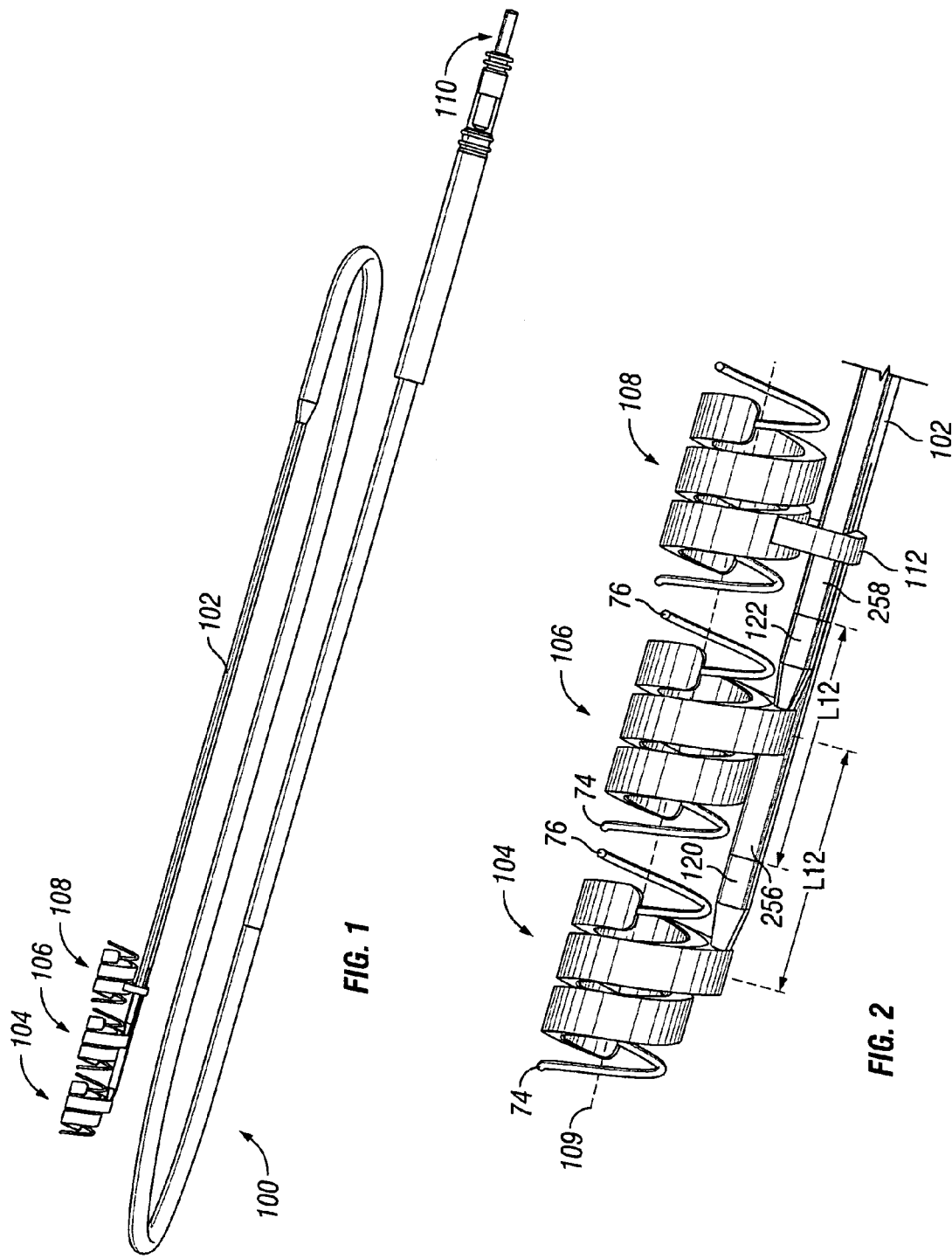

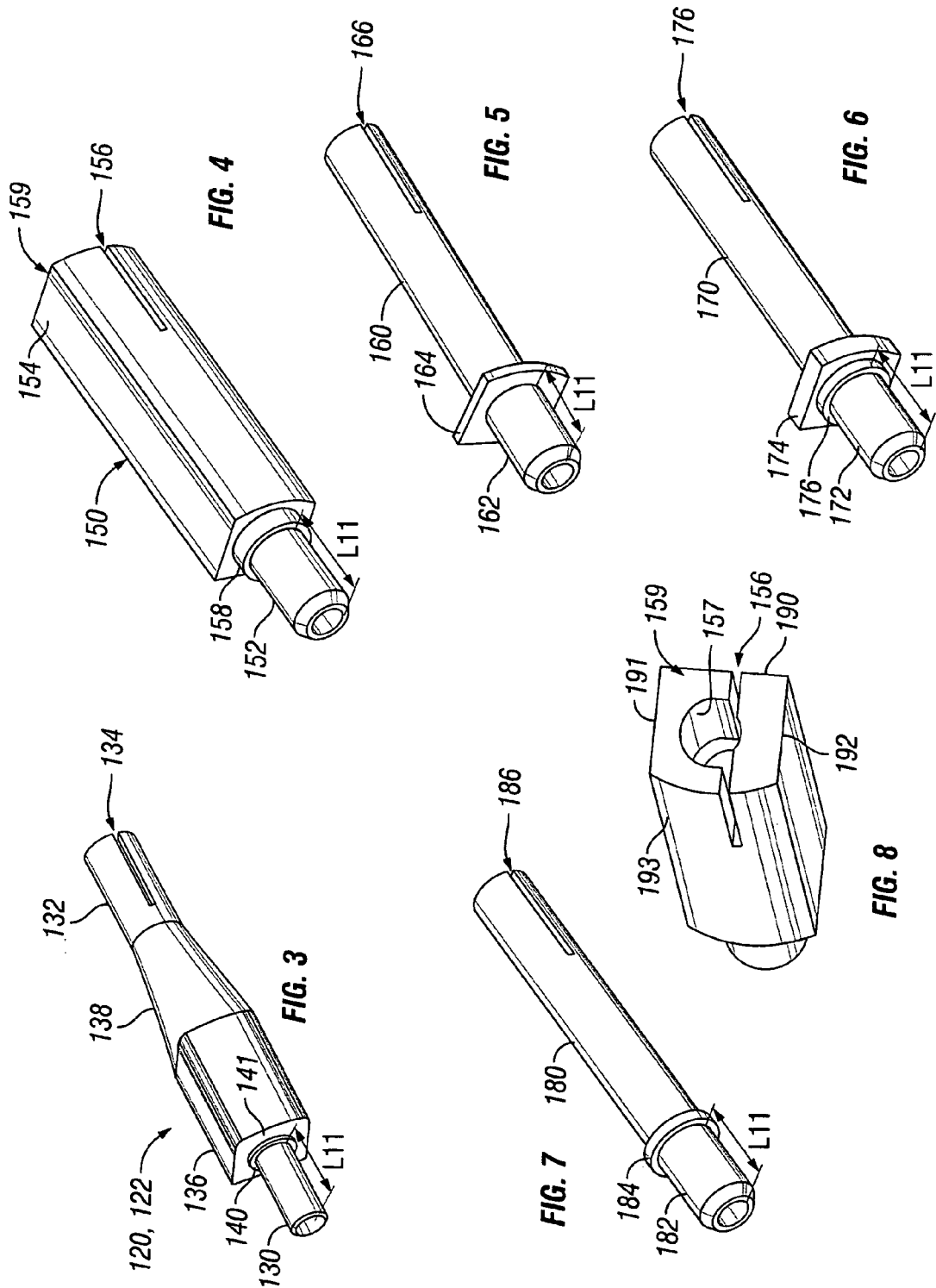

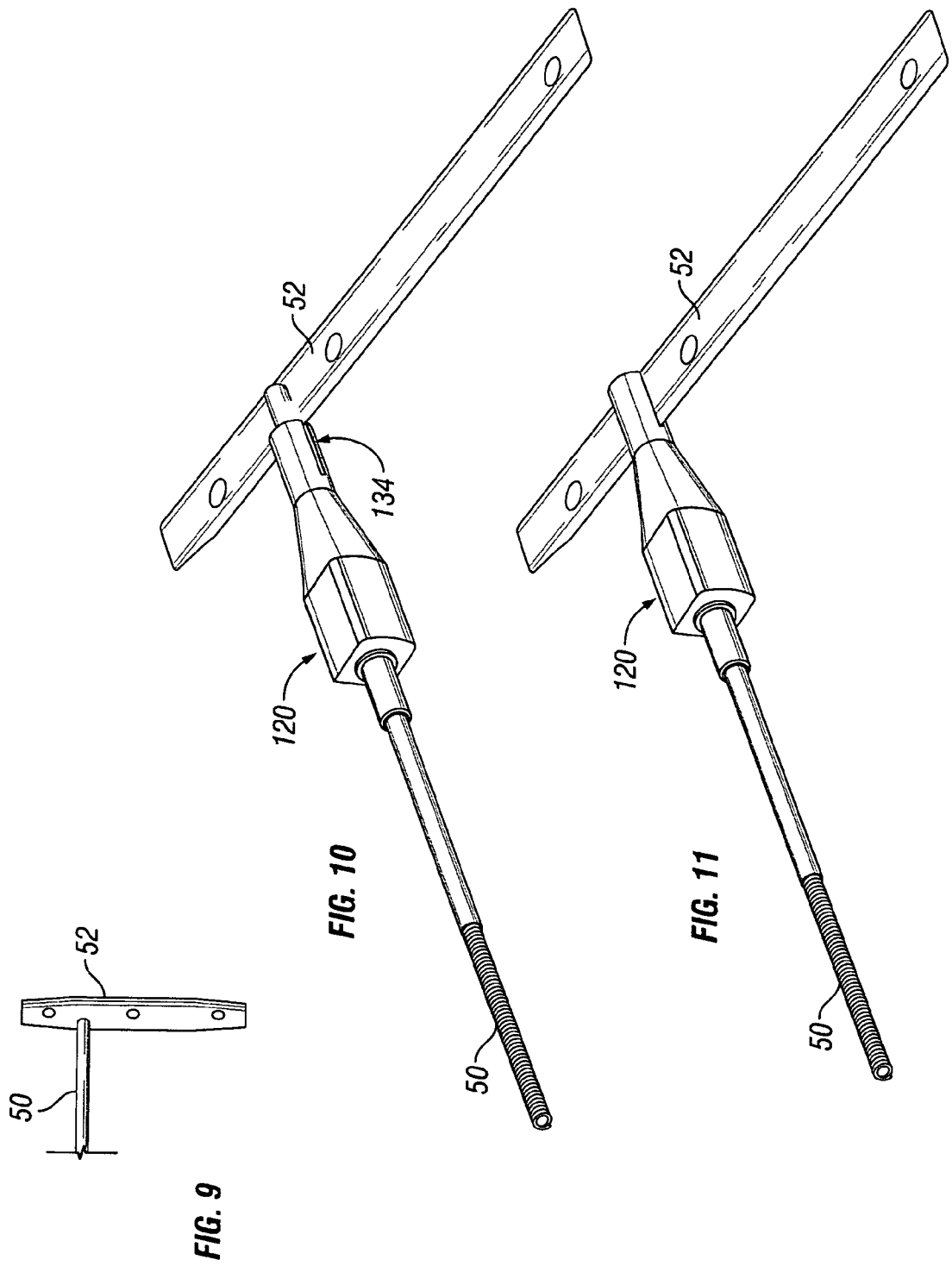

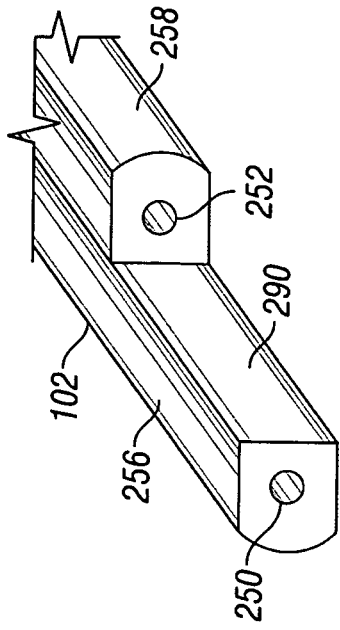
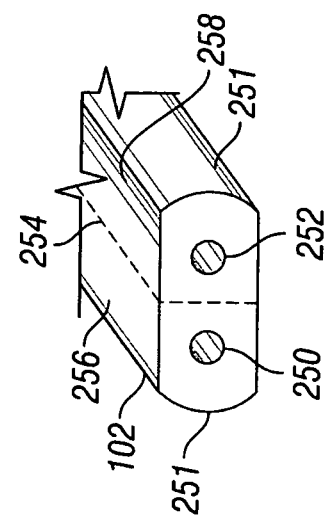
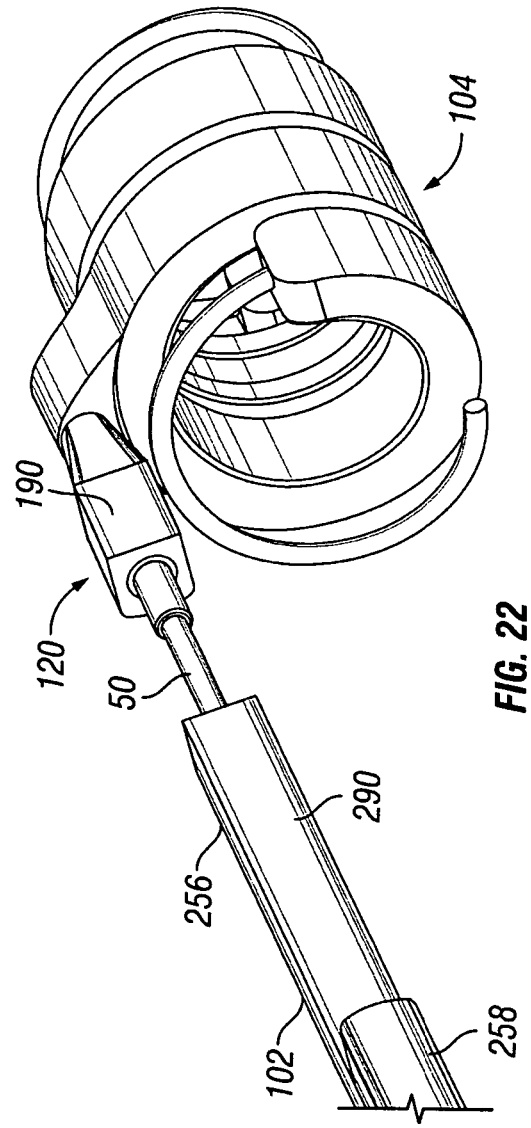

INSERT FOR IMPLANTABLE ELECTRODE

BACKGROUND

Many types of implantable medical devices, such as pacemakers, defibrillators, and vagus nerve stimulators, have leads connected to an electronics unit. The distal end of the lead typically comprises (or is coupled to) one or more conductive electrodes. Such electrodes are typically fragile and should be handled carefully by the implantation surgeon when coupling the electrode to the relevant tissue to be stimulated. Fabrication of such electrodes is a labor-intensive, time-consuming process. In some cases, a lead comprises two or more electrodes that preferably are arranged with a certain placement relative to each other. The relative placement involves both the distance separating the electrodes as well as the orientation on the lead of one electrode relative to the other. The proper spacing helps to ensure proper functioning of the associated implantable medical device. Proper orientation helps to ensure satisfactory coupling between the electrodes and the relevant body tissue. For example, helical electrodes that are to be wound about a nerve should be provided on the lead in a substantially co-linear orientation. Creating the proper relative radial and linear placement of the electrodes relative to one another on the lead during manufacturing is a painstaking and time-consuming process.

BRIEF SUMMARY

In accordance with at least some embodiments, a lead assembly comprises an outer body tubing, first and second conductors, and first and second hollow body members. The outer body tubing comprises at least two longitudinal outer body tubing portions, each such portion comprising a through-hole and each portion comprising a keyed surface having a predetermined shape. Each of the hollow body members receives a conductor and comprises a surface that substantially matches the predetermined shape of the keyed surface. When both of the conductors are inserted into corresponding longitudinal through-holes such that each of said first and second surfaces of the first and second hollow body members is substantially aligned with the keyed surface of a corresponding outer body tubing portion, electrodes formed on ends of the first and second conductors are encouraged to be in a desired relationship. In some embodiments, the electrodes are radially aligned so as to be substantially co-linear. In other embodiments, the relationship is a desired distance separating the electrodes along the length of the lead. In some embodiments, the keyed surface is substantially planar.

In accordance with another embodiment, an insert for an implantable lead comprises a hollow body member through which a conductor can be inserted. The hollow body member comprises a keyed surface and a slot formed in one end of the hollow body member. The slot is adapted to receive a conductive electrode provided on an end of said conductor. The keyed surface is adapted to be substantially aligned with a corresponding surface of a tubing into which said conductor is be inserted to facilitate manufacturing a lead assembly having a plurality of electrodes.

In accordance with another embodiment, a method of making an electrode comprises providing a first hollow body member having a first keyed outer surface, providing a first conductor and a first electrode provided on the first conductor, and positioning the first electrode in a first electrode receptacle formed in the first hollow body member. The method also comprises inserting the first conductor through a first through hole in a tubing such that the first keyed surface is substantially aligned with a first corresponding surface of the tubing to thereby orient the first electrode in a predetermined orientation with respect to the tubing.

BRIEF DESCRIPTION OF THE DRAWINGS

For a detailed description of exemplary embodiments of the invention, reference will now be made to the accompanying drawings in which:

FIG. 1 depicts a complete implantable lead assembly in accordance with embodiments of the invention;

FIG. 2 shows an enlarged view of multiple electrodes and a retaining mechanism formed on an end of the lead assembly;

FIG. 3 illustrates an embodiment of tubing insert used to form the implantable lead assembly;

FIG. 4 shows another embodiment of a tubing insert;

FIG. 5 shows yet another embodiment of a tubing insert;

FIG. 6 shows yet another embodiment of a tubing insert;

FIG. 7 shows yet another embodiment of a tubing insert;

FIG. 8 shows the opposite end of the tubing insert of FIG. 4;

FIG. 9 shows a ribbon electrode provided on a lead;

FIG. 10 shows a ribbon electrode partially inserted into a slot of a tubing insert in accordance with embodiments of the invention;

FIG. 11 shows the ribbon electrode fully inserted in the slot of the tubing insert;

FIG. 20 shows one end of the outer body tubing;

FIG. 21 shows the outer body tubing end of FIG. 20 divided into two portions, one portion being longer than the other portion, in accordance with a preferred embodiment;

FIG. 22 shows a tubing insert with a helical electrode provided therein that is partially inserted into the outer body tubing;

DETAILED DESCRIPTION

Figure 12A:
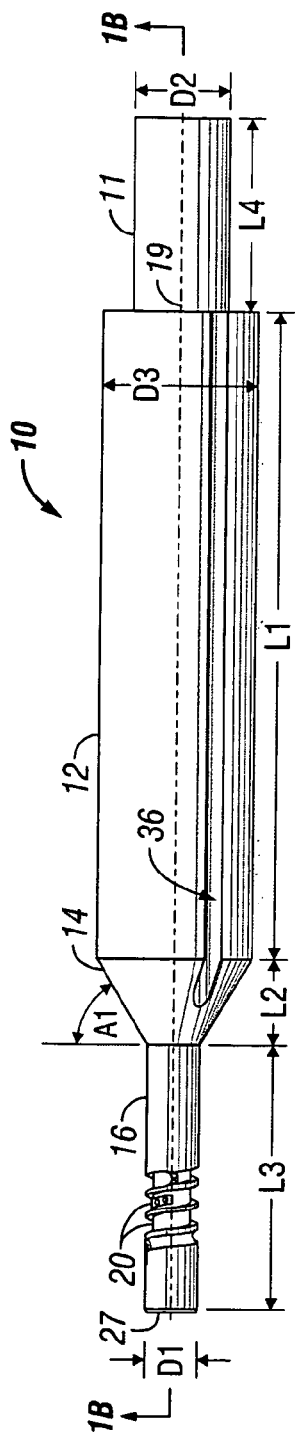
FIG. 12 shows a vacuum mandrel used to form the helical shape of each electrode in accordance with an embodiment of the invention.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and that the discussion of any embodiment is meant only to be exemplary of that embodiment, and is not intended to intimate that the scope of the disclosure, including the claims, is limited to that embodiment. Any numerical dimensions provided herein are merely exemplary and do not limit the scope of this disclosure or the claims that follow.

FIG. 1 depicts a complete implantable lead assembly 100 in accordance with a preferred embodiment of the invention. As shown, the lead assembly 100 comprises conductive electrodes 104 and 106, a lead body 102 comprising a coil and an outer body tubing or insulator, and a connector assembly 110. One or more electrically conductive electrodes 104, 106 are provided on one end of the outer body tubing 102 and a connector assembly 110 is provided on the other end of the tubing. The electrodes 104 and 106 can be formed into any suitable shape. As shown in the example of FIG. 1, the electrodes 104, 106 may be formed into a helical shape, although FIG. 2 shows an enlarged view of electrodes 104, 106 which are covered, in some embodiments, by an elastomer or other suitable insulative material. If deformed under force, the electrodes 104, 106 generally spring back to their original shape once the deformation force is removed. Such electrodes are suitable for attachment to, for example, a nerve such as vagus nerve. The electrodes 104 and 106 can be pulled in opposite directions to unravel or unfurl the electrodes for placement on the nerve using gripping surfaces 74 and 76 formed on opposing ends of the electrode as best shown in FIG. 2. During implantation, the surgeon grips the gripping surfaces 74, 76 using, for example, forceps, thereby stretching out the helical electrodes, and wraps the stretched electrodes around the nerve. Once the gripping surfaces 74, 76 are released, the elastic nature of the electrodes causes them to revert back to their original shape, leaving the electrodes to remain secured to the nerve. Although two electrodes 104, 106 are illustrated in FIGS. 1 and 2, any number of electrodes is possible, including one unipolar electrode or a multiplicity of electrodes.

Strain relief tether 108 appears similar to electrodes 104 and 106 in that it also is formed into a helical shape. Strain relief tether 108, however, preferably does not comprise a conductive electrode. Instead, it functions as a retaining mechanism coupled to the outer body tubing 102 via retaining ring 112, and is wrapped around the nerve as shown to provide strain relief. A suitable example of mechanism 108 is described in U.S. Pat. No. 4,979,511, incorporated herein by reference in its entirety.

Referring still to FIG. 1, the connector assembly 110 is electrically connected to electrodes 104, 106 via conductors disposed in and insulated by tubing 102. Each electrode 104, 106 is electrically connected to a conductor for that electrode (e.g., multiple wires wound about each other thereby forming a "coil") and each conductor runs through the length of the inside of the outer body tubing 102 and electrically connects to the contacts of pin 110. The pin 110 mates to electrical connectors of an implantable medical device (IMD) (not specifically shown) to thereby electrically couple the electrodes 104, 106 to the IMD.

The outer body tubing 102 can be made from any suitable non-conductive and non-toxic material such as silicone elastomer. The outer body tubing 102 preferably is flexible to facilitate implantation in the patient's body. The length of the outer body tubing is dictated by the location of the IMD in relation to the tissue to which the electrodes are to be attached.

It is desirable for the electrodes 104 and 106 and strain relief tether 108 to be oriented in a desired relationship relative to one another. This may include a desired radial relationship and/or a desired linear relationship relative to one another and outer body tubing 102. In one embodiment, the desired relationship is a substantially co-linear orientation as indicated by axis 109 (FIG. 2). The term "substantially co-linear" means exactly co-linear or sufficiently co-linear to allow the electrodes to attach to the nerve without damaging or causing undue stress on the nerve or electrodes due to misalignment of the electrodes coupled to a generally cylindrical nerve such as a vagus nerve in the cervical spinal area. A substantially co-linear orientation thus helps to ensure proper attachment to the nerve.

It is also desirable to maintain a prescribed linear spacing between the electrodes 104, 106 along body tubing 102 for proper functioning of the IMD to which the lead assembly 100 connects. FIG. 2 shows that the lead assembly 100 also comprises inserts 120 and 122. Each electrode 104, 106 couples to a respective insert 120, 122. As will be explained in detail below, inserts 120, 122 function to ensure proper orientation of the electrodes with respect to each other in the desired relationship. In at least one embodiment, the inserts facilitate attachment of the electrodes 104, 106 to the outer body tubing 102 in a way that causes the electrodes to be substantially co-linear. IN some embodiments the outer body tubing and/or inserts 120, 122 ensure proper spacing between the electrodes.

FIG. 3 illustrates one embodiment of a tubing insert used to form the implantable lead assembly 100. As shown in FIG. 3, insert 120 (and 122) comprises a hollow body member through which a conductor can be inserted from the electrode. One end of the hollow body member comprises an insert segment 130 that is dimensioned to fit closely within a lumen of outer body tubing 102 when inserted therein. The other end of the insert 120, 122 comprises a generally cylindrical segment 132 in which a slot is formed. The slot functions as an electrode receptacle to receive, for example, a ribbon electrode as will be explained below. The insert 120, 122 in the embodiment of FIG. 3 may also comprise segments 136 and 138. The insert 104 can be formed as a unitary structure or as separate segments mated together, for example, by welding. The inserts can be made from any suitable non-conductive material such as an elastomer. In some embodiments, the inserts are formed in a molding operation.

Insert 120, 122 of FIG. 3 also comprises a flange surface 140. When the insert segment 130 is inserted into outer body tubing 102, the end of the outer body tubing abuts flange surface 140. Flange 140 creates a gap between the end of the outer body tubing and surface 141 of the insert 120. The flange surface 140 thus creates a gap space into which an adhesive can be introduced (e.g., poured or injected) to adhere the tubing insert 120, 122 to the outer body tubing 102.

FIG. 4 shows another embodiment of a tubing insert 150. Tubing insert 150 also comprises an insert segment 152. Whereas tubing insert 120 of FIG. 3 may comprise multiple segments 136, 138 and 132, tubing insert 120 of FIG. 4 generally comprises a single segment 154. Segment 154 comprises a slot 156 for receiving an electrode. A flange surface 158 also is provided on the end opposite slot 156 to provide a gap-creating abutment surface with outer body tubing 102.

FIGS. 5 through 7 show yet additional embodiments of tubing inserts 160, 170, and 180. The inserts 160, 170 and 180 of FIGS. 5-7 comprise insert segments 162, 172 and 182, respectively, which function to be inserted into outer body tubing 102 as explained previously. Each tubing insert in FIGS. 5-7 also comprises a slot 166, 176, and 186, respectively, formed therein as shown. The embodiment of FIG. 6 also comprises a first flange surface 176 abutting a second flange surface 174 to create a gap between the outer body tubing and the insert for an adhesive to be located. In FIGS. 5 and 7, however, the outer body tubing 102 abuts against flange surfaces 164 and 184 without creating a gap. In such embodiments, an adhesive either may not be used or may partially coat the insert segments 172 and 182 to adhere to an inner surface of the lumen of the outer body tubing. The length L11 of the insert segments 130, 152, 162, 172 and 182 are predetermined so as to securely connect the insert to outer body tubing.

Referring again to FIG. 4, the tubing insert 150 comprises a slot 156 formed in end 159 as shown. FIG. 8 shows a more detailed illustration of the end 159 of the insert 150. As shown, a hollow portion 157 is formed in end 159 for receiving the coil to which the electrode is attached. The hollow portion 157 extends throughout at least some, or all, of the hollow body member comprising the insert 150.

FIG. 8 also illustrates that the tubing insert comprises four side surfaces 190-192. As can be seen in FIG. 8, in some embodiments the cross-sectional shape of the tubing insert 150 is not symmetrical. In particular, side edge 193 is curved, whereas side edges 190-192 are substantially planar. The asymmetry of tubing insert 150 is used advantageously to orient the electrode in a desired radial orientation when the electrode and associated coil are inserted into outer body tubing 102. The desired orientation in some embodiments is to locate the electrodes 104, 106 in a substantially co-linear arrangement. The asymmetry of the cross-sectional shape of the insert 150 thus functions as a "key" to facilitate assembly of the lead assembly 100. Such asymmetry is also present in the segment 136 of insert 120 (FIG. 3), flange 164 of insert 160 (FIG. 5), and second flange surface 174 of insert 170 (FIG. 6). Insert 180 has no such asymmetry and thus may not have a key characteristic.

FIG. 9 shows an electrode 52 provided on a conductor 50. In one embodiment, the conductor 50 is formed from multiple wires wound together and is referred to as a "coil." The electrode 52 preferably is an electrically conductive ribbon electrode that, when further processed as described below, can be attached to a nerve or nerve bundle such as a cranial nerve (e.g., a vagus nerve). The ribbon electrode 52 preferably is formed from platinum, platinum-iridium, or other suitable material. In a particular embodiment, the electrode 52 is approximately 0.040 inches wide by approximately 0.500 inches long by approximately 0.0005 inches thick. The electrode 52 is coupled (e.g., welded) to the conductor 50 at approximately the mid-point of the electrode.

FIGS. 10 and 11 illustrate the insertion of the coil 50 and electrode 52 combination into a tubing insert 120. In FIG. 10, the coil 50 is inserted through the end of the insert containing the slot 134, passing through the hollow body member comprising the insert and out the other end as shown. FIG. 10 illustrates that the generally flat ribbon electrode 52 slides into slot 134 of the tubing insert 120. FIG. 11 shows the ribbon electrode 52 fully inserted into slot 134.

In some embodiments, once the electrode is inserted into the slot 134 of the tubing insert 120, the electrode may be formed into the shape desired for the given application. In the embodiments depicted in this disclosure, the shape is helical, although other shapes are possible as well. FIGS. 12-19 illustrate one exemplary embodiment for forming a ribbon electrode into a helical shape.

Figure 12B:
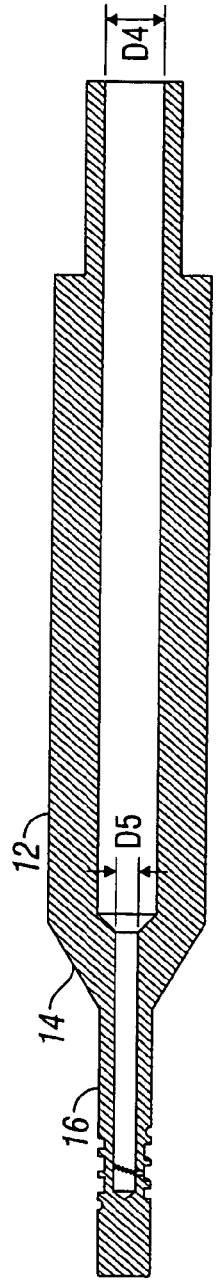
Figure 12C:
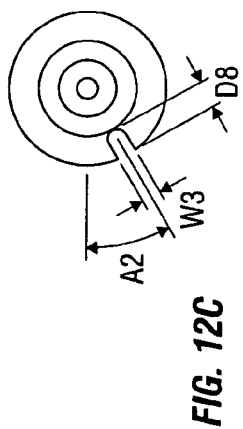

The embodiments of FIGS. 12-19 use a mandrel 10 that employs a vacuum to retain the ribbon electrode in place while an insulative material is placed over the electrode. The insulative layer helps to maintain the electrode in the desired helical shape. FIG. 12 shows a plan view of the vacuum mandrel 10 in accordance with an embodiment of the invention. The mandrel 10 comprises an elongate hollow body member formed from stainless steel or tool steel and has an exterior finish of nickel plating with Teflon®. As illustrated at the right-hand side of FIG. 12, the mandrel 10 is generally circular in cross section, although other cross-sectional shapes are possible as well. As shown, the vacuum mandrel 10 comprises a plurality of segments 12, 14, and 16. Segment 12 has a diameter D3 that, as is evident from FIG. 12, is greater than the diameter D1 of segment 16. In accordance with at least one embodiment, D1 is approximately 0.171 inches and D3 is approximately 0.50 inches. The length L1 of segment 12 preferably approximately is 2.094 inches and the length L3 of segment 16 preferably is approximately 0.875 inches. Segment 12 includes a tip portion 11 provided at one end as shown in FIG. 12. Tip portion 11 has a diameter D2 of approximately 0.312 inches and a length L4 of approximately 0.625 inches. Segment 14 has a generally frustoconical shape that transitions between segments 12 and 16. The slope of segment 14 preferably is at an angle A1 of approximately 60 degrees as shown in FIG. 12, and the length L2 of segment 14 is approximately 0.281 inches. Mandrel 10 may be formed as a unitary hollow body or in multiple pieces that are joined together in a suitable manner (e.g., by welding).

Figure 13:
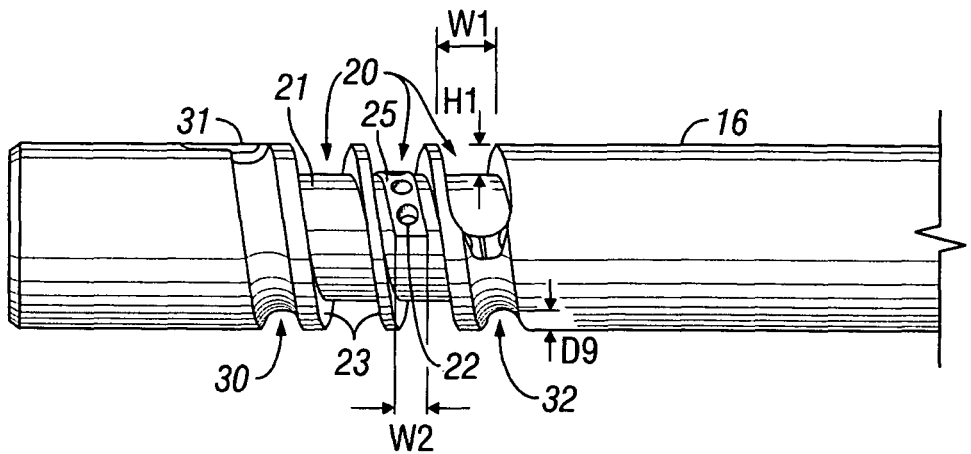
FIG. 13 shows an enlarged portion of the vacuum mandrel.
Figure 14:
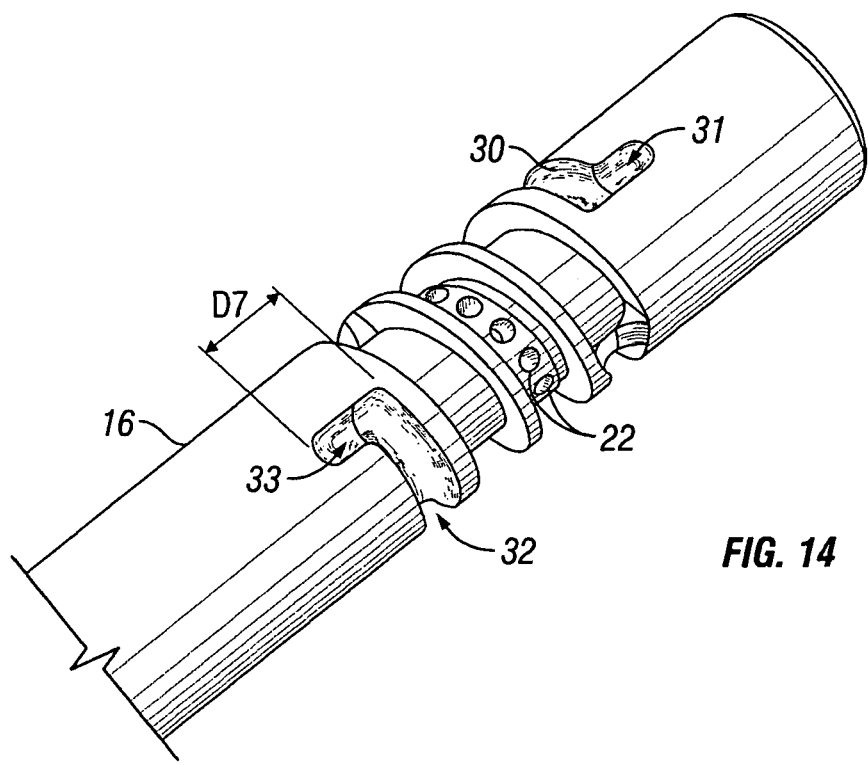
FIG. 14 shows a side of the vacuum mandrel opposite from that shown in FIGS. 12 and 13.

Segment 16 includes a first, preferably spiral (e.g., helical) groove 20 formed radially about the outer surface of segment 16 as shown in FIG. 12. FIG. 13 shows an enlarged view of segment 16 of the vacuum mandrel. In the embodiments of FIGS. 12 and 13, the first groove 20 comprises a spiral groove comprising about 2.5 revolutions around the outer surface of the mandrel. It will be appreciated by persons of skill in the art that non-spiral grooves can be used, and that where a spiral groove is employed the number of revolutions of the groove can be varied. The first groove 20 can have any dimensions that are suitable for the application described herein. In one embodiment, the groove 20 has a generally flat bottom surface 21 and flat side walls 23 formed generally perpendicular to the bottom surface 21. In this embodiment, the groove has a rectangular cross-sectional shape, with a width W1 of approximately 0.053 to 0.058 inches and a height H1 of approximately 0.024 to 0.028 inches.

As best shown in FIG. 13, a raised surface 25 is provided within groove 20. The raised surface 25 preferably is formed integrally with the segment 12 although, in other embodiments, the raised surface can be a separately formed component that is then adhered in a suitable manner (e.g., welded, glued, etc.) to surface 21. The raised surface 25 preferably has a height relative to the bottom surface 21 of approximately 0.002 to 0.003 inches and a width W2 that is less than the width W1 of the groove 20. In one embodiment, the width W2 of the raised surface 25 may range from approximately 0.028 to 0.032 inches. In such embodiments, therefore, the width W2 of the raised surface is approximately 45% to 60% of the width W1 of the first groove 20. At least one vacuum port 22 is provided within the first groove 20. In accordance with one embodiment, eight vacuum ports 22 are provided, although any number of ports sufficient to retain an electrode in place in the first groove may be employed. Preferably, the vacuum ports 22 comprise bore holes that extend through the raised surface 25 and into the hollow interior portion of segment 16. In at least one embodiment, the eight radially extending vacuum ports 22 are spaced apart in increments of 30 degrees.

Referring to FIG. 12, segment 12 of mandrel 10 comprises a lead groove 36 provided longitudinally along at least some or all of the length of segment 12. The lead groove 36 that is provided longitudinally along segment 12 relative to a plane D-D that contains central axis 19 preferably is formed in the outer surface of the segment 12 at a location disposed on an angular measure A2 from plane D-D. In one embodiment, the lead groove 36 preferably has a depth D8 of approximately 0.089 inches and a width W3 of approximately 0.063 inches.

As will be explained above, an implantable lead resides in the lead groove 36 during fabrication of an electrode. Thus, the lead groove 36 has an engaging surface that engages the electrode during manufacturing.

The interior of the hollow body member is shown in the upper portion of FIG. 12. In the embodiment depicted, the dimensions of the hollow interior of the body vary, although persons of skill in the art will appreciate that various hollow chamber designs may be employed. The hollow interior of segment 12 is shown with a diameter D4 of approximately 0.19 inches. The hollow interior of segments 14 and 16 has a diameter D5 of approximately 0.06 inches. The hollow interior of segment 16 extends to the end of, or just beyond the end of, the first groove 20. The hollow interior may also extend throughout the hollow body and be sealed off via a plug fastened by various techniques such as welding, screw threads, or adhesive.

FIGS. 12 and 13 also show one or more second grooves 30, 32 formed at, or near, opposing ends of first groove 20. Second grooves 30 and 32 may advantageously have a different cross-sectional shape than groove 20. Each second groove 30, 32 preferably is curved and extends circumferentially preferably for less than one complete revolution around segment 16 and, in some embodiments, extends for three-fourths of one revolution. As better shown in FIG. 14, each second groove 30 and 32 ends in a longitudinal groove portion 31 and 33, respectively. Each second groove 30, 32 may have a pitch of approximately from 0.65 to 0.70, a radius of curvature of approximately 0.020 inches and a depth D9 (shown in FIG. 13) of approximately 0.018 inches. Each of the longitudinal groove portions 31 and 33 may have a length D7 (FIG. 14) of approximately 0.074 inches. Further, each second groove 30, 32 begins at or near an end of the first groove 20. For example, second groove 32 begins at end 37 (FIG. 13) of first groove 20. The beginning of each second groove 30, 32 preferably is centered within first groove 20 thereby forming a continuous groove within the body segment 16. In one embodiment, each second groove 30 and 32 preferably comprises a spiral curved groove that extends for three-fourths of a revolution and the central flat-bottom groove 20 (having bottom surface 21) extends for 2.5 revolutions. Thus, the combination of the two spiral curved second grooves 30 and 32 and the central flat first groove 20 forms a groove that extends for, in a particular embodiment, four total revolutions around the body segment 16.

Figure 15:
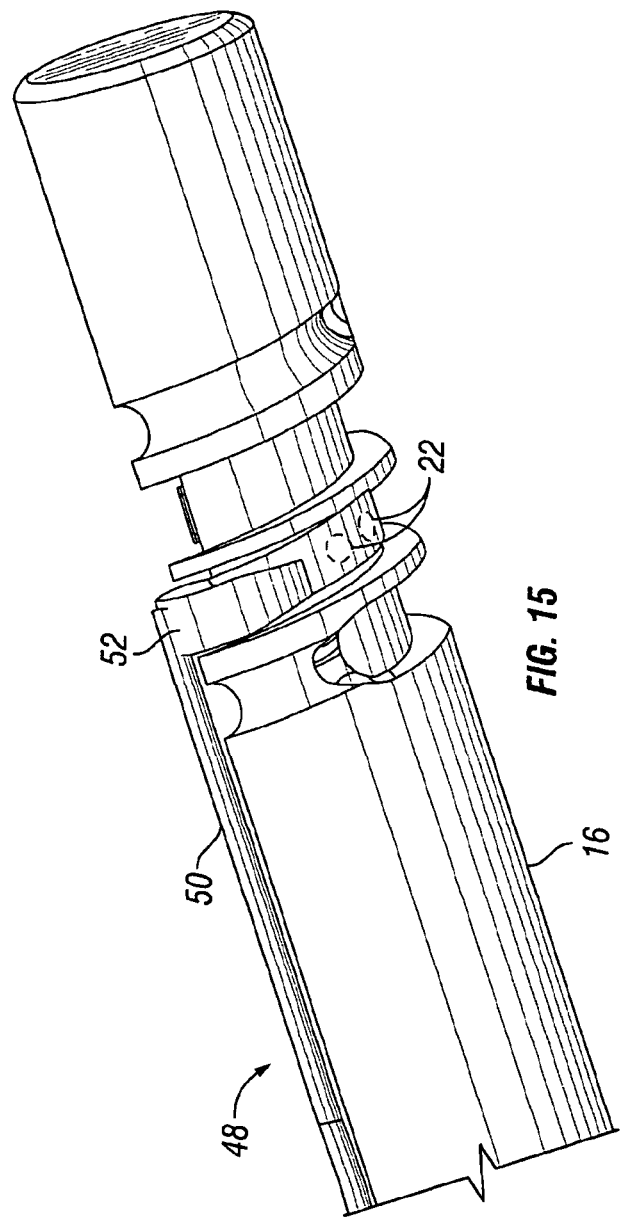
FIG. 15 shows a view of the vacuum mandrel with an electrode wrapped around a groove formed in the mandrel.

The vacuum mandrel 10 may be used during a manufacturing process for an electrode such as the electrode 52 shown in FIG. 11. FIG. 15 shows the body segment 16 of the vacuum mandrel 10 with the lead 50 and electrode 52 disposed thereon. The electrode 52 is placed on the mandrel and wrapped around and located within at least a portion of the first groove 20. By residing in the first groove 20, the ribbon electrode covers at least one or more, and preferably all, of the vacuum ports 22. FIG. 15 also shows the lead 50 extending down the length of the segment 16. The tubing insert 120 is not shown in FIG. 15, but it should be understood that the tubing insert is included with the coil 50 and electrode 52 arrangement and thus located adjacent mandrel 10. The remaining length of the lead rests in the longitudinal lead groove 36 formed in segment 12 (FIG. 12).

Figure 16:
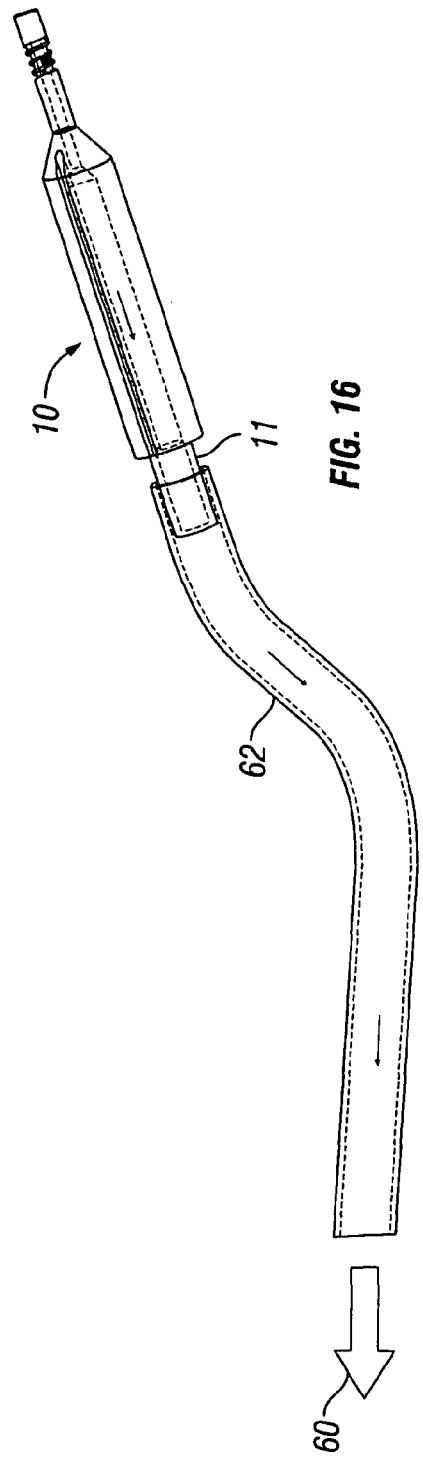
FIG. 16 illustrates the connection between the vacuum mandrel and a vacuum source.

FIG. 16 illustrates the vacuum mandrel 10 coupled to a vacuum tube 62, which, in turn, connects to a vacuum source 60. The vacuum tube 62 preferably comprises a flexible hose of rubber or other suitable material. The tip 11 of the vacuum mandrel is inserted into the vacuum tube 62. Once the vacuum source 60 is turned on, the vacuum pressure thereby created through the mandrel 10 and vacuum ports 22 will cause the ribbon electrode to be retained in place during the next part of the manufacturing process. The raised surface 25 provides an engaging surface for the electrode in groove 20 and enables the electrode edges to be encapsulated by the elastomer/insulator. In one embodiment, the vacuum pressure is approximately 28 inches mercury (Hg), although the pressure can be varied as desired.

With the electrode held in place in first groove 20 by vacuum pressure, the next step in the manufacturing process is to apply an insulator such as an elastomer to all, or substantially all, of the lengths of first groove 20, and second grooves 30 and 32, thereby covering the ribbon electrode with the insulator. The ribbon electrode 52 preferably does not extend throughout the combined lengths of first groove 20 and second grooves 30 and 32, and as such a portion of the insulator fills the grooves beyond the reach of the ribbon electrode. The insulator is applied by spraying or pouring in accordance with methods known in the art. In a particular embodiment, the insulator comprises a silicone elastomer. However, persons of skill in the art will appreciate that other elastomers, and other insulators may be used.

Figure 17:
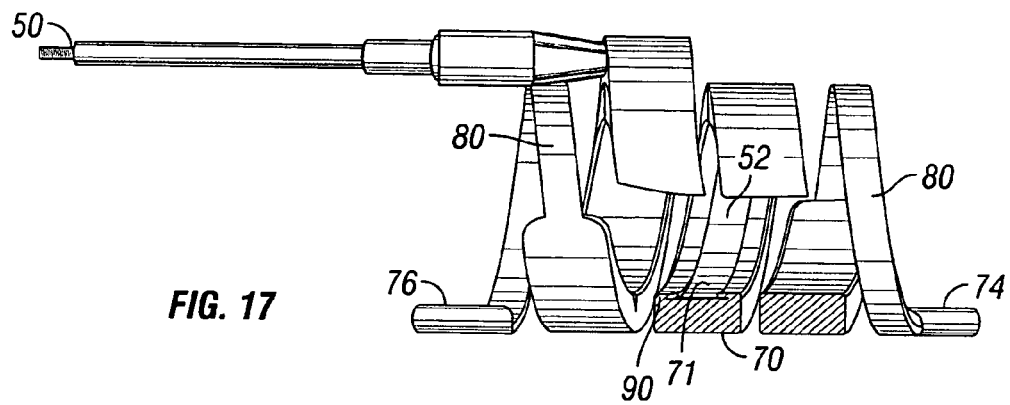
FIG. 17 shows a lead with a coil electrode formed thereon and elastomer covering a portion of the electrode.
Figure 18:
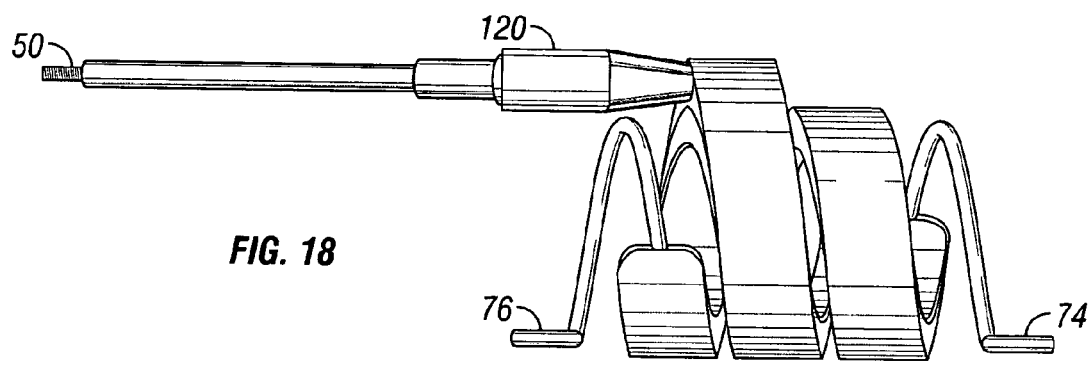
FIG. 18 shows an electrode assembly in accordance with embodiments of the invention.
Figure 19:
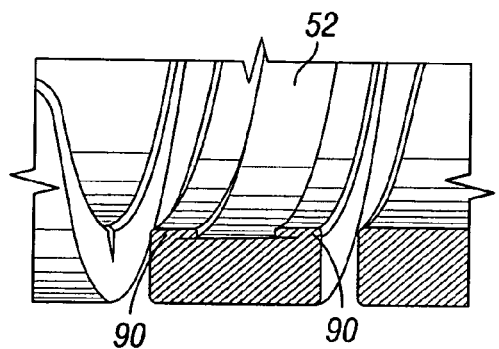
FIG. 19 shows an enlarged portion of FIG. 17.

The insulator is then permitted to cure. Once cured, the vacuum source is turned off and the lead 50 and insulator-covered electrode 52 assembly can be removed from the vacuum mandrel. Due to the shape of the mandrel, the electrodes will be formed into a helical shape. Examples of the helically formed electrodes 52 are shown in FIGS. 17 and 18. FIG. 17 shows an electrode with a cut away portion to better illustrate the elastomer 70 covering the ribbon electrode 52. Because the elastomer cured while the electrode 52 was still wrapped in the spiral first groove 20 of the vacuum mandrel, the resulting electrode generally retains the shape of the first groove 20. Other shapes are, of course, possible depending upon the needs of the particular application in which the electrode will be used. Further, because the elastomer covered the exposed electrode 52 and was not able to penetrate between the electrode 52 and the raised surface 25 of the first groove 20, one side of the electrode is not covered with elastomer, i.e., the interior surface 71 of the spirally formed electrode. This interior surface is the surface that will be in contact with the body tissue (e.g., a vagus nerve) being stimulated. The elastomer generally is an electrical insulator and thus the surface of the electrode opposite the body tissue is electrically insulated from other body tissues while the surface of the electrode touching the nerve is in electrical contact with the nerve.

The raised surface 25 on which the ribbon electrode rests while the elastomer is applied causes elastomer to fill the sides of the first groove 20 adjacent the electrode. As a result, some of the elastomer, such as that shown at reference numeral 90, covers the side edges of the ribbon electrode and thereby covers any sharp edges that might otherwise cut into the nerve to which the electrode is attached. The relationship between the elastomer and the edges of the electrode are better shown in the enlarged view of FIG. 19.

Reference numeral 80 in FIG. 17 shows the elastomer that was applied to the spiral second grooves 30 and 32. The width of second grooves 30 and 32 preferably is less than the width of first groove 20 as measured in the direction parallel to axis 19. As such, as shown in FIG. 17, the two elastomer end portions 80 of the electrode assembly are narrower than the central portion that contains the ribbon electrode.

The longitudinal groove portions 31 and 33 (FIG. 14) are also filled with elastomer. After the elastomer cures and the electrode is removed from the mandrel, the elastomer that filled the longitudinal groove portions 31 and 33 form gripping portions 74 and 76, respectively, as mentioned previously. The gripping portions 74 and 76 are used during implantation to attach the electrode to the nerve. More specifically, the gripping portions 74 and 76 are pulled in opposite directions using, for example, forceps. Pulling the gripping surfaces 74 and 76 apart in this manner stretches the spiral electrode so that it can be wrapped around the nerve. Once wrapped around the nerve, the gripping portions 74 and 76 are released and the spring-like nature of the spiral electrode 52 causes the electrode naturally to attach itself to the nerve.

FIG. 20 shows an end of the outer body tubing 102 into which the coils 50 are to be inserted. As shown, the tubing 102 comprises through holes 250 and 252. Each through hole 250 receives a coil 50. The through holes 250 and 252 preferably extend the length of the outer body tubing. In embodiments in which tubing 102 comprises two through holes (as in FIG. 20), the tubing is referred to as a "bitumen" tube. The outer edges 251 of the outer body tubing preferably are curved although other shapes are possible as well. Dashed line 254 generally denotes the approximately mid-point between the through holes 250, 252. During a manufacturing process, the outer body tubing is cut, or other suitable operation, along dashed line 254 for some, but not all, of the length of the tubing 102.

As a result of the cutting operation, the outer body tubing is divided into two portions 256 and 258. A predetermined length of one of the portions is removed (e.g., cut away). FIG. 21 illustrates the removal of part of portion 258. As a result, portion 256 is longer than portion 258. The length of portion 258 that is removed generally corresponds, or equates, to the desired spacing between the electrodes 104, 106. Further, the cutting operation along dashed line 254 results in two interior substantially planar surfaces 290 (one shown in FIG. 21) of the outer body tubing 102. Further still, each portion 256, 258 of the outer body tubing has a cross-sectional shape that is asymmetrical. In the embodiment shown in FIG. 21, one side surface 251 of each portion is curved, while the other side surfaces, including interior surface 290 are substantially planar.

Following formation of the electrode 104 into the desired shape (e.g., coil), as illustrated by FIG. 22, the coil 50 is inserted into the outer body tubing 102. The substantially planar surface 190 (FIG. 8) of the tubing insert 120 is readily aligned with the corresponding substantially planar surface 290 of the outer body tubing portion into which the coil 50 is inserted. In addition, curved side edge 193 (FIG. 8) of the tubing insert 120 may be aligned with the curved side surface 251 of the outer body tubing portion 256, 258.

Figure 23:
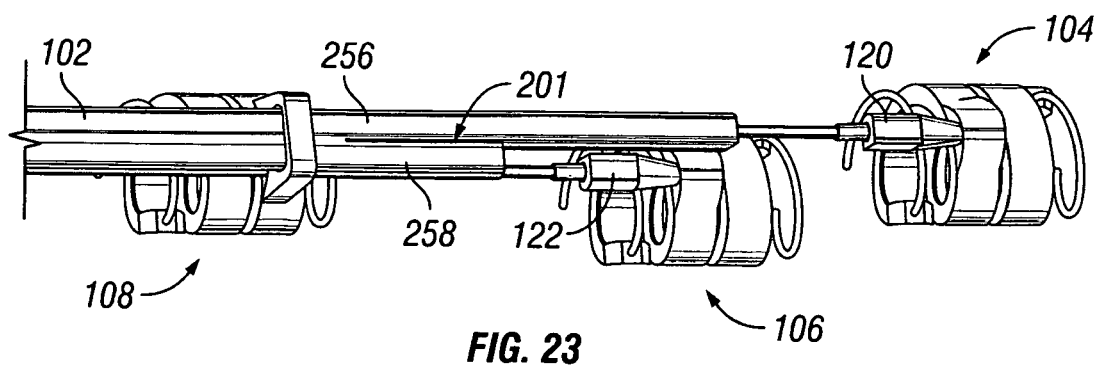
FIG. 23 illustrates two tubing inserts, each with a helical electrode, partially inserted into the outer body tubing.

FIG. 23 illustrates both coils 50 partially inserted into their respective outer body tubing portions 256 and 258. The strain relief tether 108 is placed around the outer body tubing. The cut that separates the two outer body tubing portions 256 and 258 is identified in FIG. 23 by reference numeral 201. The substantially planar surfaces 190, 191, 192 (FIG. 8) of each tubing insert are manually aligned during insertion with the corresponding substantially planar surfaces 290 of the associated outer body tubing portion 256. The curved sides 193 of each insert are similarly aligned during insertion with the corresponding curved side surface of the outer body tubing portion 256. With both inserts 120, 122 oriented so as to make their substantially planar surfaces 190 substantially co-planar with the corresponding interior planar surfaces 290 of the tubing 102, the electrodes 104, 106 will be naturally forced into a desired orientation that may be a substantially co-linear orientation. The keyed surfaces 190-192, 290 and 193, 251 of the inserts and outer body tubing 120 thus facilitate the person inserting the coils into the tubing to help ensure proper orientation of the electrodes As noted above, the two outer body tubing portions 256, 258 are of different lengths. The difference in lengths of the portions 256 and 258 is denoted by length L12 in FIG. 2. Because the tubing inserts 120, 122 are of the same length in this embodiment, the same distance L12 will separate the electrodes 104, 106.

Figure 24:
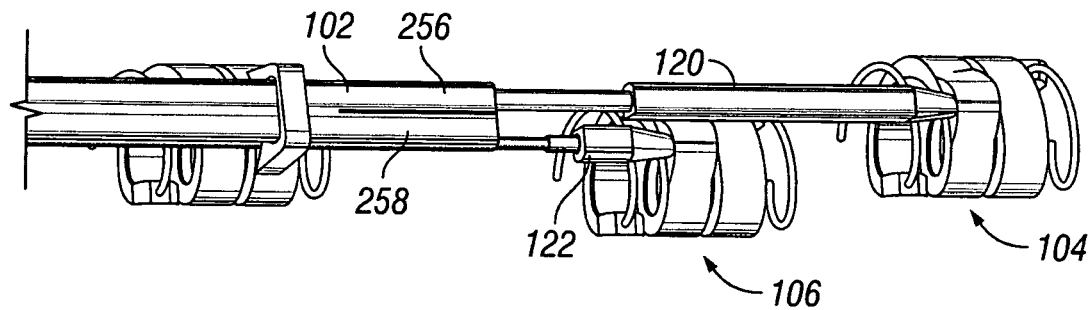
FIGS. 24 and 25 show an embodiment in which the tubing inserts are of different lengths to thereby create a desired spacing between the electrodes.
Figure 25:
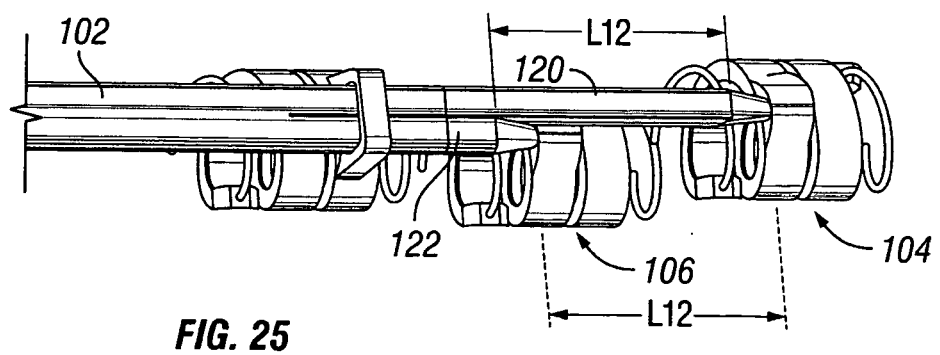

In other embodiments, such as that exemplified by FIGS. 24 and 25, the outer body tubing 102 is cut into two portions 256, 258, but the two portions are of substantially identical length. The tubing inserts 120 and 122, however, are of different lengths. In FIGS. 24 and 25, tubing insert 120 is longer than tubing insert 122. The difference in lengths of tubing inserts 120, 122 is denoted in FIG. 25 as distance L12. When the coils 50 of the associated tubing inserts and electrodes are inserted into the outer body tubing, the electrodes 104 and 106 will be spaced apart at substantially the same distance L12.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:
1. A lead assembly, comprising:
an outer body tubing comprising
a first longitudinal outer body tubing portion comprising a first through-hole and a first keyed surface having a first predetermined shape, and
a second longitudinal outer body tubing portion comprising a second through-hole and a second keyed surface having a second predetermined shape;
first and second conductors;
a plurality of electrodes with at least one electrode formed on an end of each of the first and second conductors;
a first tubing insert member that receives the first conductor, comprising a first surface having a shape that substantially matches the first predetermined shape of the first keyed surface; and
a second tubing insert member that receives the second conductor, comprising a second surface having a shape that substantially matches the second predetermined shape of the second keyed surface;
wherein, when said first conductor is inserted into said first through-hole of said first outer body tubing portion, a portion of said first tubing insert member is inserted into said first longitudinal outer body tubing portion so as to substantially align said first surface of the first tubing insert member with said first keyed surface of the first outer body tubing portion, said second conductor is inserted into said second through-hole of said second outer body tubing portion, and a portion of said second tubing insert member is inserted into said second longitudinal outer body tubing portion so as to substantially align said second surface of the second tubing insert member with said second keyed surface of the second outer body tubing portion, then the electrodes formed on ends of the first and second conductors are encouraged into a desired relationship;
wherein each of said first and second tubing insert members comprise hollow body members, each having a slot at an end of each hollow body member into which at least one of the plurality of electrodes is inserted.

2. The lead assembly of claim 1 wherein said desired relationship is a substantially co-linear relationship.

3. The lead assembly of claim 1 wherein at least one of said first and second tubing insert members comprises a flange surface that substantially abuts an end of the corresponding outer body tubing portion.

4. The lead assembly of claim 3 wherein said flange surface creates a gap at the end of the outer body tubing to receive an adhesive.

5. The lead assembly of claim 1 wherein the first and second tubing insert members are of substantially the same length and a length of one outer body tubing portion is longer than a length of another outer body tubing portion, said distance corresponding to a spacing between the electrodes.

6. The lead assembly of claim 1 wherein the first tubing insert member is of a different length than the second tubing insert member, the different length corresponds to a spacing between the electrodes.

7. The lead assembly of claim 1 wherein said first and second tubing insert members have an asymmetric cross-sectional shape.

8. The lead assembly of claim 1 wherein said predetermined shape is substantially planar.

9. The lead assembly of claim 1 wherein said first and second tubing insert members are non-conductive.

* * * * *